(12) United States Patent
Lim et al.

(10) Patent No.: US 7,892,469 B2
(45) Date of Patent: Feb. 22, 2011

(54) METHOD OF MAKING A NON-COMPLIANT BALLOON FOR A CATHETER

(75) Inventors: Florencia Lim, Union City, CA (US); NianJiong Bei, Mountain View, CA (US); Chi Le Long, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1004 days.

(21) Appl. No.: 10/802,225

(22) Filed: Mar. 16, 2004

(65) Prior Publication Data

US 2004/0173935 A1 Sep. 9, 2004

Related U.S. Application Data

(60) Division of application No. 09/733,120, filed on Dec. 8, 2000, now abandoned, which is a continuation-in-part of application No. 09/295,694, filed on Apr. 21, 1999, now Pat. No. 6,488,688, which is a continuation-in-part of application No. 09/063,969, filed on Apr. 21, 1998, now Pat. No. 6,287,314.

(51) Int. Cl.
*B29C 47/00* (2006.01)
*B29C 71/02* (2006.01)
*B29C 49/04* (2006.01)

(52) U.S. Cl. .................. 264/209.3; 264/234; 264/235; 264/210.1; 264/211.2; 264/211.12; 264/211.13; 264/345; 264/346; 264/348

(58) Field of Classification Search .............. 264/209.3, 264/33, 634, 638, 234–235; 427/2.1; 600/470; 604/96.01; 607/130

See application file for complete search history.

(56) References Cited

U.S. PATENT DOCUMENTS

| | | | |
|---|---|---|---|
| 4,003,382 A | 1/1977 | Dyke | 128/349 B |
| 4,106,509 A | 8/1978 | McWhorter | 128/349 |
| 4,265,848 A | 5/1981 | Riisch | 264/130 |
| 4,315,512 A | 2/1982 | Fogarty | 128/344 |
| 4,331,142 A | 5/1982 | Degen | 128/207 |
| 4,376,834 A | 3/1983 | Goldwasser et al. | 521/159 |
| 4,463,156 A | 7/1984 | McGary, Jr. et al. | 528/65 |
| 4,564,014 A | 1/1986 | Fogarty et al. | 128/344 |
| 4,572,186 A | 2/1986 | Gould et al. | 128/341 |
| 4,706,670 A | 11/1987 | Anderson et al. | 128/344 |
| 4,762,128 A | 8/1988 | Rosenbluth | 128/343 |
| 4,820,271 A | 4/1989 | Deutsch | 604/99 |

(Continued)

FOREIGN PATENT DOCUMENTS

EP 0 210 061 1/1987

(Continued)

*Primary Examiner*—Edmund H. Lee
(74) *Attorney, Agent, or Firm*—Fulwider Patton LLP

(57) ABSTRACT

An intravascular catheter system for properly implanting a stent in a body lumen generally comprising a catheter having an elongated shaft with an inflatable balloon formed of compliant material and a stent mounted on the working length of the balloon. The balloon material is compliant within the working range of the balloon to provide substantial radial expansion. The wingless radially expansive balloon expands in a uniform manner, thereby producing uniform expansion and implantation of the stent. Another embodiment is directed to a balloon catheter, having a semi-compliant balloon or a noncompliant balloon formed at least in part of a block copolymer.

6 Claims, 3 Drawing Sheets

U.S. PATENT DOCUMENTS

| | | | |
|---|---|---|---|
| RE32,983 E | 7/1989 | Levy | 428/36.92 |
| 4,950,239 A | 8/1990 | Gahara et al. | 604/96 |
| 5,112,304 A | 5/1992 | Barlow et al. | 604/96 |
| 5,195,969 A | 3/1993 | Wang et al. | 604/96 |
| 5,270,086 A | 12/1993 | Hamlin | 604/96 |
| 5,290,306 A | 3/1994 | Trotta et al. | 606/194 |
| 5,348,538 A * | 9/1994 | Wang et al. | 604/103.12 |
| 5,366,472 A | 11/1994 | Hillstead | 606/194 |
| 5,409,495 A | 4/1995 | Osborn | 606/108 |
| 5,415,635 A | 5/1995 | Bagaoisan et al. | 604/96 |
| 5,439,443 A | 8/1995 | Miyata et al. | 604/96 |
| 5,443,495 A | 8/1995 | Buscemi et al. | |
| 5,458,605 A | 10/1995 | Klemm | 606/108 |
| 5,470,313 A | 11/1995 | Crocker et al. | 604/96 |
| 5,492,532 A | 2/1996 | Ryan et al. | 604/96 |
| 5,498,377 A * | 3/1996 | Ozaki et al. | 264/40.1 |
| 5,500,180 A * | 3/1996 | Anderson et al. | 264/532 |
| 5,500,181 A * | 3/1996 | Wang et al. | 264/532 |
| 5,556,383 A | 9/1996 | Wang et al. | 604/96 |
| 5,628,754 A | 5/1997 | Shevlin et al. | 606/108 |
| 5,643,278 A | 7/1997 | Wijay | 606/108 |
| 5,645,560 A | 7/1997 | Crocker et al. | 606/192 |
| 5,669,880 A | 9/1997 | Solar | 604/96 |
| 5,681,522 A * | 10/1997 | Roychowdhury | 264/532 |
| 5,707,354 A | 1/1998 | Salmon et al. | 604/96 |
| 5,738,901 A | 4/1998 | Vickerman et al. | |
| 5,743,874 A | 4/1998 | Fischell et al. | 604/96 |
| 5,752,934 A | 5/1998 | Campbell et al. | 604/96 |
| 5,766,203 A | 6/1998 | Imran et al. | 606/198 |
| 5,769,817 A | 6/1998 | Burgmeier | 604/96 |
| 5,772,669 A | 6/1998 | Vrba | 606/108 |
| 5,776,140 A | 7/1998 | Cottone | 606/108 |
| 5,780,573 A * | 7/1998 | Iwata et al. | 528/272 |
| 5,792,144 A | 8/1998 | Fischell et al. | 606/108 |
| 5,792,300 A | 8/1998 | Querns et al. | |
| 5,807,520 A | 9/1998 | Wang et al. | 264/520 |
| 5,833,706 A | 11/1998 | St. Germain et al. | 606/194 |
| 5,868,704 A | 2/1999 | Campbell et al. | 604/96 |
| 5,968,069 A | 10/1999 | Dubabek et al. | 606/194 |
| 6,146,356 A | 11/2000 | Wang et al. | 604/96 |
| 6,395,208 B1 * | 5/2002 | Herweck et al. | 264/127 |
| 6,656,550 B1 * | 12/2003 | Zamore | 428/35.7 |
| 2004/0093008 A1 * | 5/2004 | Zamore | 606/194 |

FOREIGN PATENT DOCUMENTS

| | | | |
|---|---|---|---|
| EP | 0 357 562 | | 3/1990 |
| EP | 0 357 562 A1 | | 3/1990 |
| EP | 0 540 858 | | 5/1993 |
| EP | 0 553 960 | | 8/1993 |
| EP | 0 592 885 | | 4/1994 |
| EP | 0 592 885 A2 | | 4/1994 |
| EP | 0 745 395 | | 12/1996 |
| EP | 0 745 395 A2 | | 12/1996 |
| EP | 0 778 037 | | 6/1997 |
| EP | 0 778 037 A1 | | 6/1997 |
| WO | WO 95/23619 | | 9/1995 |
| WO | WO 96/37240 | | 11/1996 |
| WO | WO 98/03218 | * | 1/1998 |
| WO | WO 98/05377 | | 2/1998 |

* cited by examiner

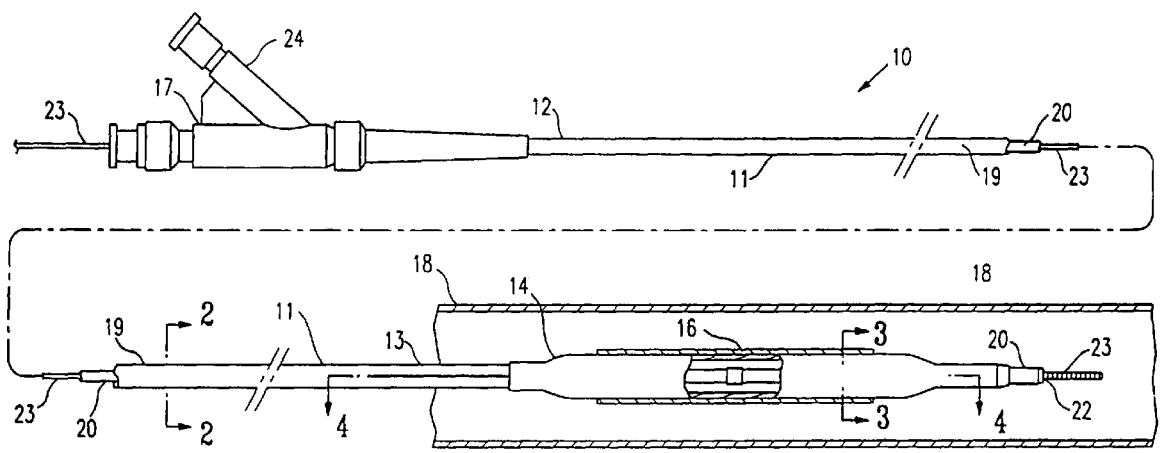
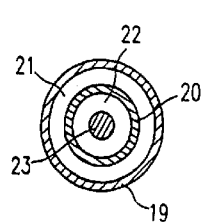
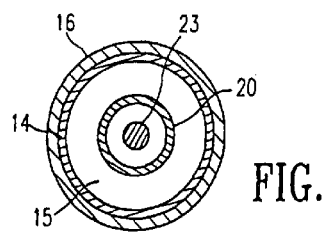
FIG. 1
FIG. 2
FIG. 3

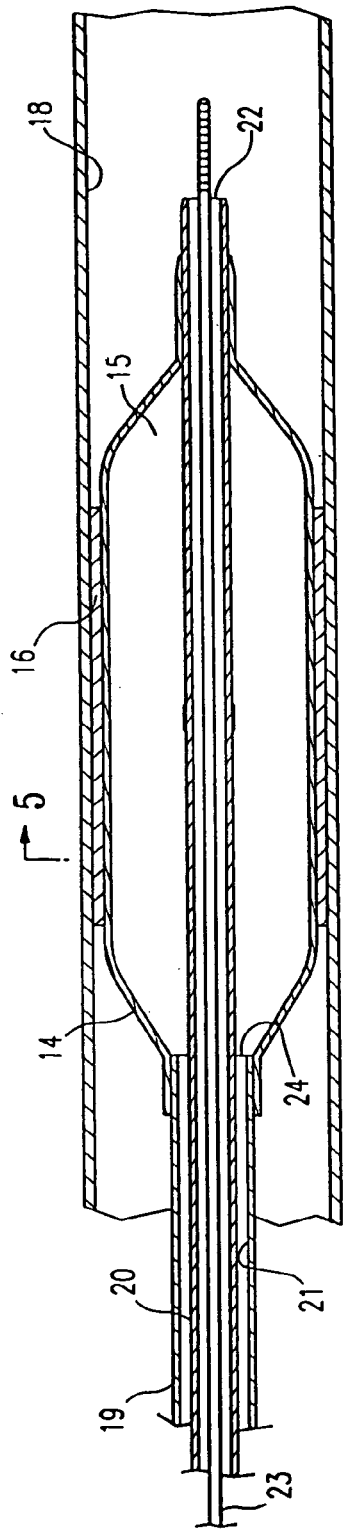
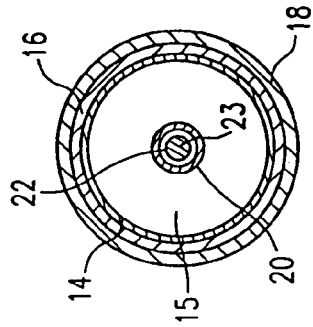
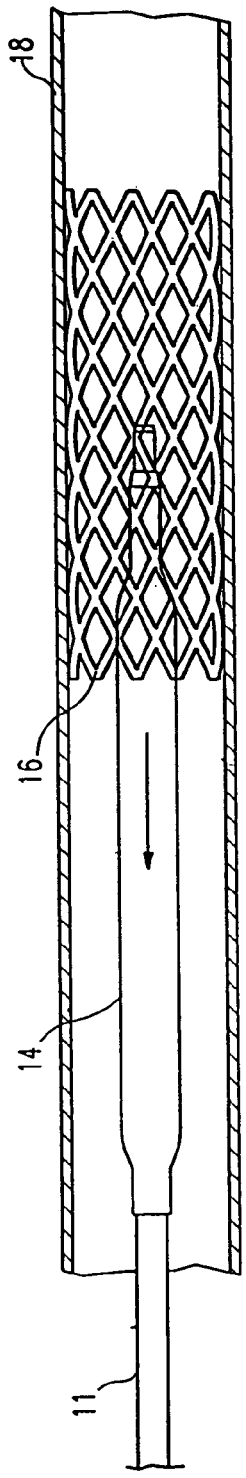
FIG. 4
FIG. 5
FIG. 6

METHOD OF MAKING A NON-COMPLIANT BALLOON FOR A CATHETER

This application is a divisional of application Ser. No. 09/733,120 filed Dec. 8, 2000 now abandoned which is a continuation-in-part application of Ser. No. 09/295,694, filed Apr. 21, 1999, now U.S. Pat. No. 6,488,688 which is a continuation-in-part application of Ser. No. 09/063,969, filed Apr. 21, 1998, now U.S. Pat. No. 6,287314.

BACKGROUND OF THE INVENTION

The invention relates to the field of intravascular catheters, and more particularly to a balloon catheter.

In percutaneous transluminal coronary angioplasty (PTCA) procedures a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference. Thus, stents are used to open a stenosed vessel, and strengthen the dilated area by remaining inside the vessel.

In conventional stent deploying balloon catheters, the balloon is made of essentially non-compliant material, such as nylon or polyethyleneterephthalate (PET). Such non-compliant material exhibits little expansion in response to increasing levels of inflation pressure. Because the non-compliant material has a limited ability to expand, the uninflated balloon must be made sufficiently large that, when inflated, the balloon has sufficient working diameter to compress the stenosis and open the patient's passageway. However, a large profile non-compliant balloon can make the catheter difficult to advance through the patient's narrow vasculature because, in a uninflated condition, such balloons form flat or pancake shape wings which extend radially outward. Consequently, the wings of an uninflated balloon are typically folded into a low profile configuration for introduction and advancement through the vessel. The wings are again produced upon deflation of the balloon following stent deployment within the patient. These wings on the deflated balloon are undesirable because they result in an increased balloon profile which can complicate withdrawing the catheter after stent deployment.

Although stents have been used effectively for some time, the effectiveness of a stent can be diminished if it is not properly implanted within the vessel. For example, expansion of a balloon folded into a low profile configuration for introduction into the patient, can cause nonuniform expansion of a stent mounted on the balloon. The nonuniform expansion of conventional designs has resulted in the use of an elastic sleeve around the balloon and under the stent to distribute force from the expanding folded balloon to the stent uniformly, see for example U.S. Pat. No. 5,409,495 (Osborn), which is incorporated herein by reference. However, such sleeves may fail to completely prevent the nonuniform expansion of the stent, they increase the deflated profile upon insertion into the patient, and they complicate the assembly of the stent onto the balloon. Additionally, the final location of the implanted stent in the body lumen may be beyond the physician's control where longitudinal growth of the stent deploying balloon causes the stent's position on the balloon to shift during deployment. As the balloon's axial length grows during inflation, the stent may shift position along the length of the balloon, and the stent may be implanted upstream or downstream of the desired location in the body lumen. Thus, balloons which have a large amount of longitudinal growth during inflation provide inadequate control over the location of the implanted stent.

Therefore, what has been needed is an improved catheter balloon. The present invention satisfies these and other needs.

SUMMARY OF THE INVENTION

The invention is directed to a catheter balloon having improved performance due to a desired degree of balloon compliance The term compliance as used herein should be understood to refer to the radial compliance of the balloon unless otherwise stated. One embodiment of the invention is directed to a stent delivery system with a stent deploying balloon formed of compliant material that uniformly expands the stent to properly implant the stent within the patient's body lumen. Another embodiment is directed to a balloon catheter having a balloon exhibiting semi-compliance or non-compliance, and a method of making the balloon.

The stent delivery system of the invention generally comprises a catheter having an elongated shaft with an inflatable balloon on a distal portion of the catheter and a stent disposed about the working length of the balloon. The balloon is formed of material compliant at least within a working range of the balloon, and which therefore provides for substantially uniform radial expansion within the working range. The compliant balloon material therefore expands substantially elastically when pressurized at least within the pressure range disclosed herein for use in inflating the stent deploying balloon of the invention. The compliant balloon material will generally be an highly elastic material. The term "compliant" as used herein refers to thermosetting and thermoplastic polymers which exhibit substantial stretching upon the application of tensile force. Additionally, compliant balloons transmit a greater portion of applied pressure before rupturing than non-compliant balloons. Suitable compliant balloon materials include, but are not limited to, elastomeric materials, such as elastomeric varieties of latex, silicone, polyurethane, polyolefin elastomers, such as polyethylene, flexible polyvinyl chloride (PVC), ethylene vinyl acetate (EVA), ethylene methylacrylate (EMA), ethylene ethylacrylate (EEA), styrene butadiene styrene (SBS), and ethylene propylene diene rubber (EPDM). The presently preferred compliant material has an elongation at failure at room temperature of at least about 250% to at least about 500%, preferably about 300% to about 400%, and a Shore durometer of about 50A to about 75D, preferably about 60A to about 65D.

When the stent delivery balloon of the invention is pressurized, the balloon expands radially in a uniform manner to a working diameter. Because the balloon expands uniformly without unwrapping wings, it will uniformly expand a stent mounted on the balloon. The uninflated balloon does not require folding into a low profile configuration for insertion into the patient or the use of elastomeric sleeves used with conventional stent deploying balloons made from relatively non-compliant material. Similarly, the balloon of the invention should have a substantial elastic recoil so that it deflates into a smaller diameter with little or no wings. The undesirable flat or pancake shape wings which form when conventional stent deploying balloons are deflated are thus avoided. Additionally, minimal axial growth of the balloons during inflation provides improved control over the placement of the implanted stent in the body lumen. The compliant balloon results in improved abrasion and puncture resistance relative to the conventional non-compliant stent deploying balloons at least in part because there is little or no movement between the balloon and stent when the balloon expands radially. Moreover, due to the compliant nature of the balloon, there is a more highly efficient transfer of force to the stent than with the high pressure non-compliant conventional balloons which expend much expansive force to overcome rigidity (non-compliance) and to size the stent.

In another embodiment, the balloon catheter having a semi-compliant balloon generally comprises a catheter having an elongated shaft with an inflatable balloon on a distal portion of the shaft. The semi-compliant balloon is formed at least in part of a block copolymer, such as a polyurethane block copolymer. The term semi-compliant should be understood to mean a balloon with low compliance, which therefore exhibits moderate stretching upon the application of tensile force. The semi-compliant balloon has a compliance of less than about 0.045 millimeters/atmospheres (mm/atm), to about rupture, in contrast to compliant balloons such as polyethylene balloons which typically have a compliance of greater than 0.045 mm/atm. The percent radial expansion of the balloon, i.e., the growth in the balloon outer diameter divided by the nominal balloon outer diameter, at an inflation pressure of about 150 psi (10.2 atm) is less than about 4%. Another embodiment of the invention comprises a noncompliant balloon, preferably formed at least in part of a polyurethane block copolymer, which has a compliance of not greater than about 0.025 mm/atm.

In a presently preferred embodiment, the semi-compliant or noncompliant balloon is formed of a polyurethane block copolymer. Suitable polyurethane block copolymers include polyether based polyurethanes such as PELLETHANE available from Dow Plastics, polyester based polyurethanes such as PELLETHANE available from Dow Plastics and ESTANE available from BF Goodrich, polyether based aromatic polyurethanes such as TECOTHANE available from Thermedics, polyether based aliphatic polyurethanes such as TECO-PHILIC available from Thermedics, polycarbonate based aliphatic polyurethanes such as CARBOTHANE available from Thermedics, polycarbonate based aromatic polyurethanes such as BIONATE available from The Polymer Technology Group (PTG), solution grade polyurethane urea such as BIOSPAN available from PTG, and polycarbonate-silicone aromatic polyurethane such as CHRONOFLEX available from Cardiotech. Other suitable block copolymers may be used including TEXIN TPU available from Bayer, TECOPLAST available from Thermedics, and ISOPLAST available from Dow.

One aspect of the invention is directed to a catheter balloon which is axially noncompliant. The terminology "axially noncompliant" should be understood to mean a balloon having a length which exhibits little or no axial growth during inflation of the balloon. The axially noncompliant balloon has an axial compliance of less than about 0.25 mm/atm, to about rupture. The length of the balloon increases by less than about 2.5% to about 20% over an inflation pressure range of about 60 psi (4 atm) to about 315 psi (21 atm), and by less than about 5% to about 15% within an inflation pressure range of about 90 psi (6 atm) to about 205, psi (14 atm). The balloon therefore avoids the trauma to the vessel wall caused when ends of an axially elongated balloon expand against a portion of the vessel wall. The invention also includes a method of making a semi-compliant balloon. The method generally comprises extruding a tubular product formed at least in part of a block copolymer, such as a polyurethane block copolymer. The extruded tubular product is heated to a first elevated temperature and the outer diameter of the tubular product is expanded to a second outer diameter. While still under pressure, the expanded tubular product is heated at a second elevated temperature. The second elevated temperature is equal to or greater than the first elevated temperature. The expanded, heat-treated tubular product is then cooled to form the semi-compliant balloon. The tubular product is preferably heated to the first and second elevated temperatures by locally heating the tubular member with a heating member displaced along a length of the tubular product. The resulting balloons are semi-compliant, and axially noncompliant with low axial growth during inflation. The invention also includes a method of making a noncompliant balloon.

The semi-compliant block copolymer balloon of the invention provides improved performance due to the strength and softness of the balloon, with controlled expansion at relatively high pressures, and without the stiffness or poor refold characteristics of noncompliant balloons. Moreover, the low axial growth of the balloon during inflation provides improved control over the dilatation of a stenosis or implantation of a stent.

These and other advantages of the invention will become more apparent from the following detailed description of the invention and the accompanying exemplary drawings.

BRIEF DESCRIPTION OF THE DRAWINGS

FIG. 1 is an elevational view partially in section of a catheter system which embodies features of the invention, showing the balloon and stent in an unexpanded state.

FIG. 2 is a transverse cross sectional view of the catheter system of FIG. 1 taken along lines 2-2.

FIG. 3 is a transverse cross sectional view of the catheter system of FIG. 1 taken along lines 3-3.

FIG. 4 is an elevational view partially in section of the distal section of the catheter system of the invention as shown in FIG. 1 depicting the balloon and stent expanded.

FIG. 5 is a transverse cross sectional view of the expanded balloon and stent of FIG. 4 taken along lines 5-5.

FIG. 6 illustrates the catheter system shown in FIG. 1, depicting the balloon in a deflated state and the stent implanted within the patient's lumen.

DETAILED DESCRIPTION OF THE INVENTION

Figure 7:
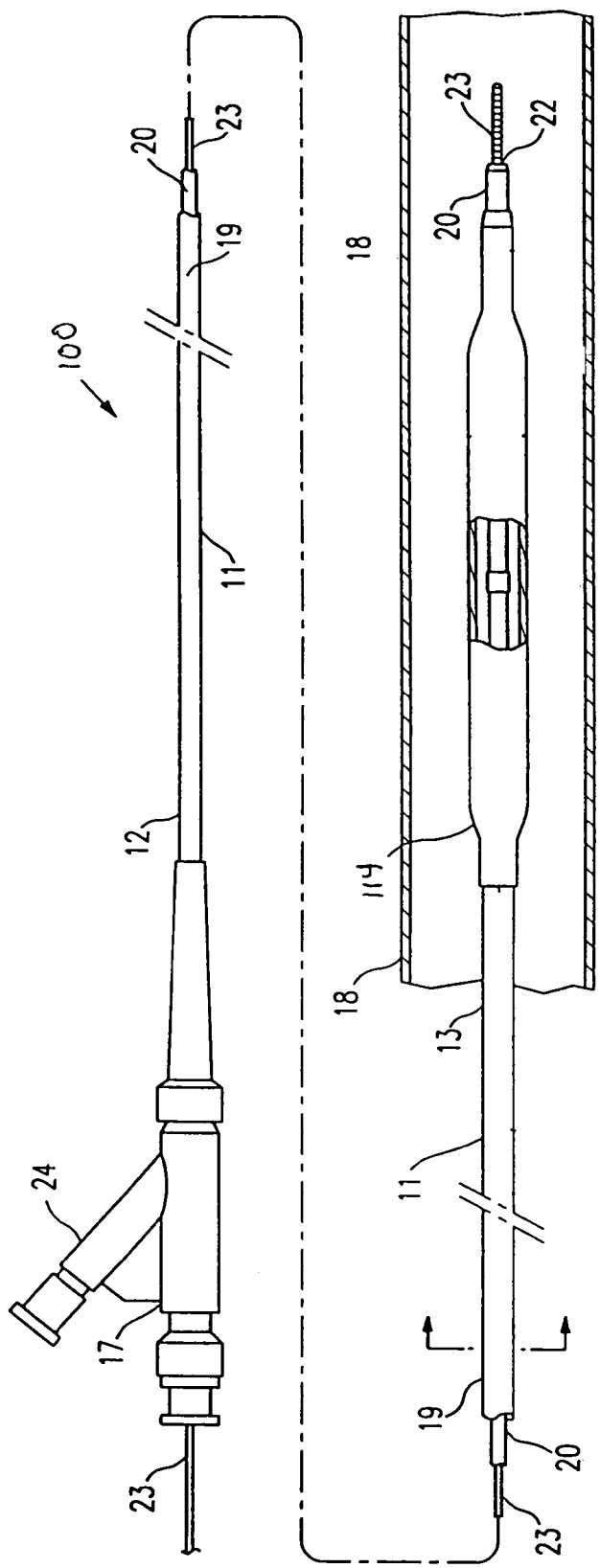
FIG. 7 illustrates a balloon catheter having a semi-compliant balloon which embodies features of the invention.

FIG. 1 illustrates an intravascular catheter system which embodies features of the invention for implanting a stent in a body lumen. The catheter system of the invention generally includes a catheter 10 having an elongated catheter shaft 11 having a proximal 12 and distal 13 section, a radially expansive inflatable balloon 14 on the distal section 13 of the catheter shaft 11, a stent 16 mounted on the balloon 14, and an adapter 17 mounted on the proximal section 12 of shaft 11.

In FIG. 1, the catheter system is illustrated within a patient's body lumen 18, with the stent 16 in an unexpanded state prior to expansion of the balloon 14. The inflatable balloon 14 is formed of radially expansive material that is compliant within the working range of the balloon. As best illustrated in FIG. 3, the compliant balloon is essentially wingless and does not require folding into a low profile configuration for insertion into the patient. FIG. 4 illustrates the balloon in an expanded state during stent deployment. FIG. 5 illustrates a transverse cross section of the balloon illustrated in FIG. 4 taken along lines 5-5.

In the embodiment illustrated in FIG. 1, the catheter shaft 11 has an outer tubular member 19 and an inner tubular member 20 disposed within the outer tubular member and defining, with the outer tubular member, inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19.

The balloon 14 may be formed of any compliant material, and includes thermoplastic and thermosetting polymers. The presently preferred compliant polymeric materials providing a wingless balloon with substantially elastic recoil during deflation include polyurethanes such as TECOTHANE from Thermedics. TECOTHANE is a thermoplastic, aromatic, polyether polyurethane synthesized from methylene diisocyanate (MDI), polytetramethylene ether glycol (PTMEG) and 1,4 butanediol chain extender. TECOTHANE grade 1065D is presently preferred, and has a Shore durometer of 65D, an elongation at break of about 300%, and a high tensile strength at yield of about 10,000 psi. However, other suitable grades may be used, including TECOTHANE 1075D, having a Shore D of 75. Balloons produced from the TECOTHANE materials are particularly preferred because the axial growth of the balloon during inflation in minimized, and the axial and radial size of the balloon deflates to the original preinflation size following inflation and deflation of the balloon. Thus, inflation produces little or no axial or radial growth, so that the deflated balloons elastically recoil to the preinflation size. Other suitable compliant polymeric materials which deflate so that at least the radial size of the balloon returns to the original preinflation radial size, and which therefore have a substantially elastic recoil after deflation, include ENGAGE from DuPont Dow Elastomers (an ethylene alpha-olefin polymer) and EXACT, available from Exxon Chemical, both of which are thermoplastic polymers and are believed to be polyolefin elastomers produced from metallocene catalysts. Other suitable compliant materials include, but are not limited to, elastomeric silicones, latexes, and urethanes. The type of compliant material may be chosen to provide compatibility with the catheter shaft material, to thereby facilitate bonding of the balloon to the catheter.

The stent deploying balloon of the invention can be produced by conventional techniques for producing catheter inflatable members, and may be preformed by stretching a straight tube formed of the compliant material or formed in situ after attachment to the catheter shaft. Because the compliant material provides substantial radial expansion, the balloon need not be preformed, unlike non-compliant stent deploying balloons, so that production of the compliant balloon catheter of the invention is simplified relative to conventional non-compliant balloon catheters.

FIG. 2, showing a transverse cross section of the catheter shaft 11, illustrates the guidewire receiving lumen 22 and inflation lumen 21. The balloon 14 can be inflated by radiopaque fluid from an inflation port 24, from inflation lumen 21 contained in the catheter shaft 11, or by other means, such as from a passageway formed between the outside of the catheter shaft and the member forming the balloon, depending on the particular design of the catheter. The details and mechanics of balloon inflation vary according to the specific design of the catheter, and are well known in the art.

The compliant balloon has sufficient strength to withstand the inflation pressures needed to inflate the balloon and expand the stent mounted thereon. The burst pressure of the compliant balloon (about 3.0 mm) is about 10 atm to about 15 atm, and the tensile strength of an American Standard Testing Method (ASTM) "dog-bone" sample cut from a compression molded sheet of material is about 3000 psi to about 7500 psi. The hoop strength, e.g. the product of the burst pressure and the balloon diameter, divided by two times the balloon wall thickness, of a 3.0 mm balloon of the invention is about 10,000 psi to about 20,000 psi. The hoop strength of a 2.5 mm balloon formed from TECOTHANE 1065D is about 18,000 psi. The inflation pressure needed to expand a stent varies depending on the balloon material and stent material and design, but is generally about 6 atm to about 8 atm.

The compliant material may be cross linked or uncrosslinked, depending upon the balloon material and characteristics required for a particular application. The presently preferred polyurethane balloon materials are not crosslinked. However, other suitable materials, such as the polyolefinic polymers ENGAGE and EXACT, are preferably crosslinked. By crosslinking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure, and thereby avoid overexpanding the stent to an undesirably large diameter.

The catheter shaft will generally have the dimensions of conventional dilatation or stent deploying catheters. The length of the catheter 10 may be about 90 cm to about 150 cm, and is typically about 135 cm. The outer tubular member 19 has a length of about 25 cm to about 40 cm, an outer diameter (OD) of about 0.039 in to about 0.042 in, and an inner diameter (ID) of about 0.032 in. The inner tubular member 20 has a length of about 25 cm to about 40 cm, an OD of about 0.024 in and an ID of about 0.018 in. The inner and outer tubular members may taper in the distal section to a smaller OD or ID.

The length of the compliant balloon 14 may be about 1 cm to about 4 cm, preferably about 1.5 cm to about 3.0 cm, and is typically about 2.0 cm. In an uninflated or deflated state the balloon diameter is generally about 0.015 in (0.4 mm) to about 8 in (2 mm), and is typically about 0.037 in (1 mm), and the wall thickness is generally about 0.004 in (0.1 mm) to about 0.016 in (0.4 mm), and is typically about 0.008 in (0.2 mm). In an expanded state, the balloon diameter is generally about 0.06 in (1.5 mm) to about 0.18 in (4.5 mm), and the wall thickness is about 0.0005 in (0.012 mm) to about 0.0025 in (0.06 mm).

Various designs for dilatation catheters well known in the art may be used in the catheter system of the invention. For example, conventional over-the-wire dilatation catheters for angioplasty usually include a guidewire receiving lumen extending the length of the catheter shaft from a guidewire port in, the proximal end of the shaft. Rapid exchange dilatation catheters generally include a short guidewire lumen extending to the distal end of the shaft from a guidewire port located distal to the proximal end of the shaft.

When delivering a stent into a patient, the catheter 10 is inserted into a patient's vasculature to the desired location which is shown in FIGS. 1 and 4 as a dilated stenotic region, and inflation fluid is delivered through the inflation lumen 21 to the compliant balloon 14 through the inflation port 24. Because of the balloon's compliant material, it expands radially. Longitudinal growth can be prevented by the inner tubular member 20 or by stretching or axial orientation during processing. Consequently, the stent 16 mounted on the balloon expands uniformly. When the inflation fluid is removed, the balloon 14 retracts to a wingless shape from elastic recoil to allow the catheter to be withdrawn. The stent remains in place in the patient's body lumen, as illustrated in FIG. 6, showing the deflated balloon 14 and expanded stent 16 within the body lumen 18. The stent 16 may be any of a variety of stent materials and forms designed to be implanted by an expanding member, see for example U.S. Pat. No. 5,514,154 (Lau et al.) and U.S. Pat. No. 5,443,500 (Sigwart), incorporated by reference. For example, the stent material may be stainless steel, a NiTi alloy, a Co—Cr—Mo containing alloy such as MP-35N, a plastic material, or various other materials. The stent has a smaller diameter for insertion and advancement into the patient's lumen which may be formed by contracting the stent or by folding at least a portion of the stent into a wrapped configuration.

EXAMPLE 1

TECOTHANE 1065D was used to prepare balloon tubing having a mean ID of about 0.0195 inch (0.5 mm) and a mean OD of about 0.0355 inch (0.9 mm), and the balloon tubing was used to prepared balloons having an OD of about 2.5 mm. The mean balloon OD was about 0.110 inch (2.8 mm), and mean dual wall thickness was about 0.0015 inch (0.038 mm). The mean rupture pressure was about 238 psi, and the mean hoop strength was about 18,000 psi. Radial (OD) and axial (length) compliance measurements were made on the unrestrained balloons. The term unrestrained refers to a balloon with one end attached to an inflation medium source and the other end clamped shut, as opposed to a balloon with proximal and distal ends secured to a catheter shaft. The balloons have a substantially uniform radial expansion, as illustrated in Table 1, which lists the average balloon OD for the unruptured balloons, at a given inflation pressure, for five balloons tested. The balloons also have minimal axial growth during inflation, as illustrated in Table 2, which lists the average working length for the unruptured balloons, of five balloons tested, at a given inflation pressure. The axial growth, to rupture, of the balloons is about 32% to about 35% of the original, uninflated 20 mm working length. Moreover, this axial lengthening would be expected to be less in a secured balloon having proximal and distal ends secured to a catheter shaft.

TABLE 1

| Inflation Pressure (PSI) | Average Balloon OD (MM) |
|---|---|
| 30 | 2.476 |
| 45 | 2.743 |
| 60 | 2.917 |
| 75 | 3.044 |
| 90 | 3.148 |
| 105 | 3.239 |
| 120 | 3.324 |
| 135 | 3.405 |
| 150 | 3.482 |
| 165 | 3.560 |
| 180 | 3.634 |
| 195 | 3.709 |
| 210 | 3.776 |
| 225 | 3.853 |
| 240 | 3.996 |
| 255 | 4.089 |

TABLE 2

| Inflation Pressure (PSI) | Average Balloon Working Length (MM) |
|---|---|
| 30 | 20.6 |
| 45 | 21.4 |
| 60 | 22.4 |
| 75 | 22.8 |
| 90 | 23.6 |
| 105 | 24.1 |
| 120 | 24.5 |
| 135 | 24.9 |
| 150 | 25.4 |
| 165 | 25.6 |
| 180 | 26.1 |
| 195 | 26.5 |
| 210 | 26.5 |
| 225 | 26.75 |
| 240 | 27 |
| 255 | 27 |

Figure 8:
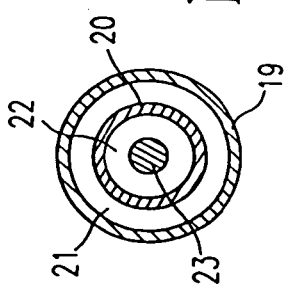
FIG. 8 illustrates a transverse cross section of the balloon catheter shown in FIG. 7, taken along lines 8-8.
Figure 9:
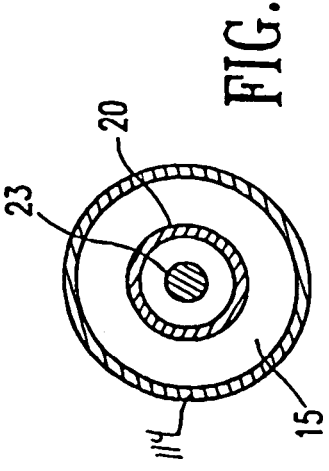
FIG. 9 illustrates a transverse cross section of the balloon catheter shown in FIG. 7, taken along lines 9-9.

FIG. 7 illustrates another embodiment of the invention generally Comprising a balloon catheter having a balloon which exhibits not greater than semi-compliant expansion. The balloon catheter 100 is similar in many respects to the balloon catheter 10 illustrated in FIG. 1, with similar components being identified with the same reference numerals. In one embodiment, the balloon catheter has a semi-compliant balloon. The catheter generally includes an elongated shaft 11 having a proximal section 12, a distal section 13, a semi-compliant balloon 114, and an adapter 17 mounted on the proximal section of the shaft. The catheter includes an outer tubular member 19, inner tubular member 20, inflation lumen 21, and guidewire lumen 22, as outlined above. In a presently preferred embodiment, the balloon 114 typically forms wings, which may be folded into a low profile configuration (not shown) for introduction into and advancement within the patient's vasculature. FIGS. 8 and 9 illustrate transverse cross sections of the balloon catheter shown in FIG. 7, taken along lines 8-8 and 9-9, respectively. To the extent not discussed herein, the dimensions and uses of the catheter 100 having a semi-compliant balloon 114 are similar to those described for catheter 10.

In one embodiment of the invention, the balloon 114 exhibits semi-compliant expansion. The semi-compliant balloon 114 expands a moderate amount, less than a compliant balloon but more than a noncompliant balloon, in response to increasing inflation pressure. The semi-compliant balloon 114 preferably exhibits not less than semi-compliant expansion, so that the balloon preferably has a compliance of not less than 0.025 mm/atm over the desired inflation pressure range. The balloon 114 has a compliance of less than about 0.045 mm/atm, and preferably from about 0.025 to about 0.04 mm/atm, over an inflation pressure range of about 30-90 psi (2-6 atm) to about 285 psi (19.4 atm). The percent radial expansion is less than about 4%, and preferably from about 1.5% to about 4%, at an inflation pressure of about 150 psi (10.2 atm).

The semi-compliant balloon 114 is formed from a block copolymer. In a presently preferred embodiment, the block copolymer is a polyurethane block copolymer. The Shore durometer hardness of the block copolymer is about 80A to about 82D, preferably about 55D to about 75D. The flexural modulus of the block copolymer is about 10,000 to about 370,000 psi, preferably about 150,000 to about 300,000 psi. One presently preferred polyurethane is PELLETHANE grade 2363, which is an ether based polyurethane elastomer having a Shore durometer hardness of 75D. However, other suitable grades may be used, including but not limited to PELLETHANE 2363 having a Shore durometer hardness of 55D or 65D may also be used. PELLETHANE 2363 is a polytetramethylene glycol based polyurethane, synthesized from aromatic diisocyanate and short chain diol chain extenders such as butanediol. In a presently preferred embodiment, the rupture pressure of the balloon is about 265 psi to about 450 psi. The working range, or pressure at which the balloon is typically inflated within the body, is about 90 psi to about 285 psi.

The balloon embodying features of the invention is axially noncompliant, and exhibits minimal axial growth as the pressure is increased during inflation. The balloon has low axial growth of less than about 5% to about 20% over the working range of the balloon (about 90 psi to about 285 psi), and an axial compliance of about 0.1 mm/atm to about 0.25 mm/atm within an inflation pressure range of about 90 psi to about 205 psi. The length of the balloon increases by less than about 5% to about 10% at an inflation pressure of about 150 psi (10.2 atm).

The semi-compliant balloon 114 of the invention is made according to a method of the invention. In a method of making a semi-compliant balloon, balloon tubing comprising a block copolymer extruded into a tubular product is radially expanded to form the balloon by heating the tubular product at a first elevated temperature and subjecting the tubular product to an expansion pressure. The balloon is typically formed within a mold having dimensions close to the dimensions of the desired balloon. The blow up ratio, i.e., the balloon outer diameter divided by the balloon tubing inner diameter, is typically about 5.0 to about 8.0, and preferably about 7.0 to about 8.0. The tubular product may also be axially elongated by stretching before, during, or after being radially expanded. In a presently preferred embodiment, to heat the tubular product to the first elevated temperature during the radial expansion, a heating member such as a heat nozzle is displaced along a length of the tubular product within the mold, to thereby apply heat to portions of the tubular product adjacent to the heating member. The expanded tubular product is then heat treated at a second elevated temperature which is equal to or greater than the first elevated temperature, by displacing the heating member along a length of the tubular product from one end of the balloon to the other end. The first temperature is about 80° C. to about 120° C., and preferably about 95° C. to about 105° C. The second temperature is about 100° C. to about 140° C., and preferably about 110° C. to about 140° C. (measured in mold temperature). In a presently preferred embodiment, the second temperature is greater than the first temperature. The second temperature is typically no more than about 10° C. to about 50° C., preferably no more than about 10° C. to about 20° C., greater than the first temperature. In one embodiment, a balloon having a 3.0 mm nominal outer diameter heat treated at a second elevated temperature equal to or above the first elevated temperature and having a blow up ratio of about 7 to about 8, inflates to the 3.0 mm outer diameter at about 6 atm to about 7 atm, and has a ¼ outer diameter size increase at about 13 atm to about 14 atm for a blow up ratio of about 7, and about 18 atm to about 20 atm for a blow up ratio of about 8. The heating member is typically displaced at a rate that is less than the rate at which heating member was displaced during the expansion of the tubular product. The balloon is then cooled within the mold under pressure.

Semi-compliant balloons were prepared according to the method of the invention, as set forth in the following examples.

EXAMPLE 2

Balloons having a nominal OD of about 3.0 mm, and a length of about 20 mm were prepared using the method of the invention. PELLETHANE 75D was used to prepare balloon tubing having an ID of about 0.015 inch (0.381 mm) to about 0.0195 inch (0.495 mm), and an OD of about 0.031 inch (0.787 mm) to about 0.036 inch (914 mm). The balloon tubing was heated and stabilized at 40° C. for 16 to 24 hours prior to being blown into balloons. The balloon tubing was then placed in a balloon mold and stretched axially, and the mold was heated to a wall temperature of about 100-120° C. To expand the balloon tubing, the tubing was heated to a blow temperature of about 100° C., by displacing a heat nozzle at about 1 mm/sec to about 5 mm/sec from one end of the mold to the opposite end, while pressurizing the tubing at an expansion pressure of about 220 psi to about 270 psi. The expanded tubing was then heat treated within the mold and at the expansion pressure, at a heat treating temperature equal to, or about 10° C. to about 20° C. greater than the blow temperature by displacing the heat nozzle from one end of the mold to the opposite end at a slower speed than the speed used during the blowing, of about 1.0 mm/sec to about 2.0 mm/sec. The pressurized balloon was then cooled to room temperature within the mold. The resulting balloons had a percent radial expansion of about 1.5 to about 4.0%, an elastic stress response, i.e., growth in balloon OD at about 5 atm after inflation to about 10 atm divided by the initial balloon OD at about 5 atm, of about 0.25%, and a wall tensile strength of about 15,000 to about 16,000 psi.

EXAMPLE 3

PELLETHANE 75D was used to prepare balloon tubing having an ID of about 0.017 inch (0.43 mm) and an OD of about 0.032 inch (0.8 mm), and the balloon tubing was used to prepared a balloon having a nominal OD of about 3.0 mm using the method of the invention as outlined above, in which the expanded tubing was heat treated at a temperature greater than the blowing temperature. The rupture pressure was about 300 psi to about 350 psi. Radial (OD) and axial (length) compliance measurements were made on the unrestrained balloon. The term "unrestrained" refers to a balloon with one end attached to an inflation medium source and the other end clamped shut, as opposed to a balloon with proximal and distal ends secured to a catheter shaft. The balloon has a semi-compliant radial expansion, as illustrated in Table 3, which lists the balloon OD for the unruptured balloon, at a given inflation pressure. The compliance of the balloon over a pressure range of about 30 psi to about 300, or to about the rupture pressure, is 0.037 mm/atm. The balloon also has minimal axial growth during inflation, as illustrated in Table 4, which lists the working length for the unruptured balloons at a given inflation pressure. The axial growth, to rupture, of the balloons is about 25% of the original, uninflated 20 mm working length. Moreover, this axial lengthening would be expected to be less in a secured balloon having proximal and distal ends secured to a catheter shaft.

TABLE 3

| Inflation Pressure (PSI) | Balloon OD (MM) |
| --- | --- |
| 30 | 2.674 |
| 45 | 2.757 |
| 60 | 2.835 |
| 75 | 2.901 |
| 90 | 2.951 |
| 105 | 2.995 |
| 120 | 3.034 |
| 135 | 3.068 |
| 150 | 3.099 |
| 165 | 3.127 |
| 180 | 3.155 |
| 195 | 3.183 |
| 210 | 3.208 |
| 225 | 3.231 |
| 240 | 3.257 |
| 255 | 3.279 |
| 270 | 3.302 |
| 285 | 3.326 |
| 300 | 3.35 |

TABLE 4

| Inflation Pressure (PSI) | Balloon Working Length (MM) |
| --- | --- |
| 30 | 20.5 |
| 45 | 20.5 |
| 60 | 21 |
| 75 | 21 |
| 90 | 21.5 |
| 105 | 21.5 |
| 120 | 22 |
| 135 | 22 |
| 150 | 22.5 |
| 165 | 22.5 |
| 180 | 23 |
| 195 | 23 |
| 210 | 23 |
| 225 | 23.5 |
| 240 | 24 |
| 255 | 24 |
| 270 | 24 |
| 285 | 24.5 |
| 300 | 25 |

In another embodiment, the balloon catheter 100 has a noncompliant balloon 114 formed of a block copolymer. The noncompliant balloon is similar in many respects to the semi-compliant balloon but with a compliance of about 0.025 mm/atm or less over the working range of the balloon, or about 8% to about 12% of the 3.0 mm outer diameter of a 3.0 mm outer diameter balloon, over a working pressure range of about 7 atm to about 20 atm of the balloon (i.e., the growth in the balloon outer diameter divided by 3.0 mm). The noncompliant balloon is made according to a method similar to the method used to make the semi-compliant balloon. In one embodiment, the blow up ratio of the balloon greater than about 8. Generally, the blow up ratio used in preparing the noncompliant balloon of the invention is greater than about 7 to greater than about 8, depending on the polymeric material used. Preferably, the blow up ratio is greater than 7 for a balloon formed of Pellethane 2363. For a balloon formed of Bionate polycarbonate polyurethane, the blow up ratio is greater than about 6, preferably greater than about 7, and for improved balloon fatigue resistance, most preferably 7.6 to about 8.

In one presently preferred embodiment, the noncompliant balloon is formed of a polycarbonate polyurethane such as Bionate® having an elongation at break of at least about 250%, with a compliance of not greater than about 0.02 mm/atm, and preferably about 0.012 to about 0.016 mm/atm over the working pressure range of the balloon. A presently preferred Bionate® polycarbonate polyurethane comprises the product of the reaction of poly(1,6-hexyl 1,2-ethylcarbonate) diol and 4,4'-methylene bisphyenyl diisocyanate (MDI), and a chain extender such as 1,4-butane diol. Preferably, the noncompliant balloon comprising Bionate® polycarbonate polyurethane is formed from balloon tubing annealed at about 50° C. to about 60° C., and preferably about 50° C. to about 55° C., for about 16 to about 24 hours. Preferably, the blow up ratio is about 7.4 to about 7.8. Other polycarbonate polyurethanes including aliphatic diisocyanate based polyurethanes such as Carbothane® have been found to be not preferred in making the noncompliant balloon of the invention, due at least to the low rupture pressure and high compliance of the balloons as compared to balloons formed from Bionate®. The rupture pressure of the balloon is at least about 18 atm, and preferably greater than about 18 atm.

EXAMPLE 4

A radially and axially noncompliant balloon was formed of a polycarbonate polyurethane. The polycarbonate polyurethane was Bionate® grade 75D, available from PTG, having an aromatic isocyanate hard segment such as 4,4'-methylene bis(phenyl isocyanate) (MDI), and a polycarbonate diol soft segment such as poly(1,6-hexyl carbonate) diol (PHCD), and a butanediol chain extender. The Bionate® polyurethane is prepared by reacting the polycarbonate diol which gives rise to the soft segments in the polyurethane with an aromatic isocyanate, and reacting the resulting prepolymer with the chain extender. The Shore Durometer hardness of the Bionate® is preferably about 65D or higher, and most preferably about 75D or higher. The molecular weight is about 100,000 to about 500,000 Dalton, preferably about 175,000 to about 300,000 Dalton. Bionate® grade 75D having a Shore Durometer hardness of about 75D has a flexural modulus of 307,000 psi, an ultimate tensile strength of about 7000 to about 9,100 psi, and an ultimate elongation of about 255% to about 320%. The Bionate® grade 75D was used to extrude balloon tubing having an outer diameter of about 0.031 inch to about 0.034 inch and an inner diameter of about 0.015 inch to about 0.018 inch. The extruded tubing is preferably not crosslinked. The balloon tubing was annealed at 55° C. for 16 hours. After annealing the balloon tubing was expanded in a mold and heat set in the mold as outlined in Example 2, except the blow up ratio of the balloon was 7.6. The resulting balloon had an outer diameter of 3.0 mm, a working length of 20 mm, and a dual wall thickness of about 1.5 to about 1.8 mils (0.038 to 0.045 mm). The balloon had a radial compliance of about 0.015 mm/atm from 7 to 22 atm (and about 0.016 mm/atm after e-beam sterilization), and about 0.011 mm/atm from about 20 atm to about 27 atm. The balloon had an axial growth of 0.75 mm from about 9 to 18 atm. The axial growth was about 4% of the original 20 mm working length of the balloon, from 9 to 18 atm. The working pressure range is about 7 to about 18 psi, the mean rupture pressure was about 27 atm, and the fatigue at 18 atm was about 95% reliability. A similar balloon prepared by annealing the balloon tubing at 40° C. for 16 hours while otherwise using the same procedure outlined above had axial growth of 7.5% to 10%.

It will be apparent from the foregoing that, while particular forms of the invention have been illustrated and described, various modifications can be made without departing from the spirit and scope of the invention. For example, while the balloon catheter illustrated in FIGS. 1 and 7 has inner and outer tubular members with independent lumens, a single tubular membered shaft having two lumens therein may also be used. Although individual features of embodiments of the invention may be described or shown in some of the drawings and not in others, those skilled in the art will recognize that individual features of one embodiment of the invention can be combined with any or all the features of another embodiment. Other modifications may be made without departing from the scope of the invention.

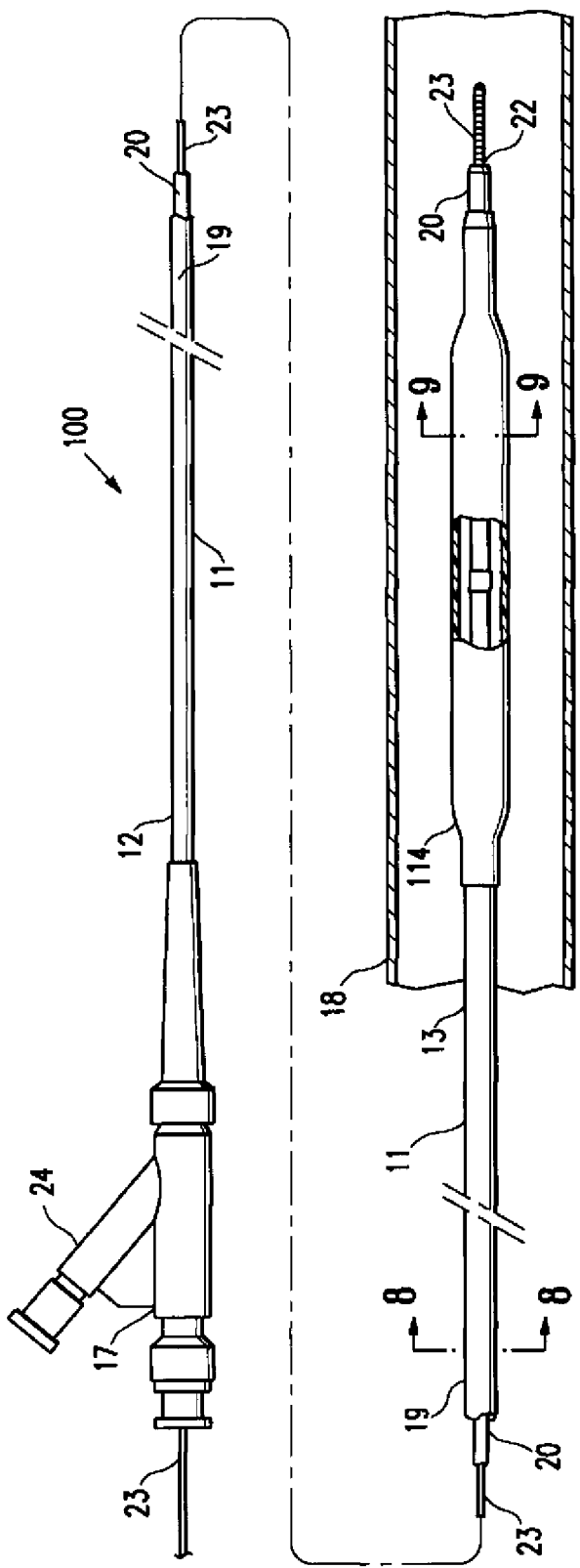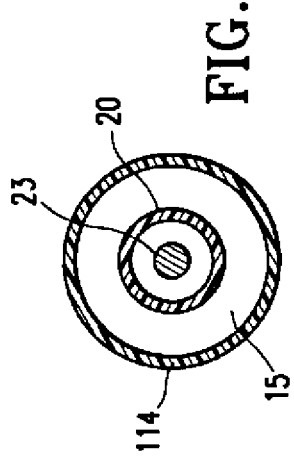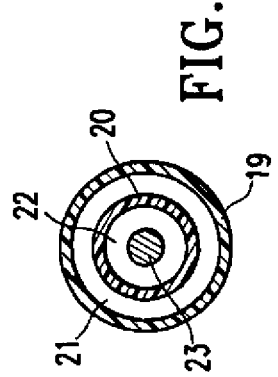

What is claimed is:

1. A method of making a radially and axially noncompliant balloon for a catheter, comprising
   a) first extruding a tubular product formed at least in part of a block copolymer, having a first outer diameter and a first inner diameter;
   b) then, prior to any expansion, annealing the tubular product at not less than about 50° C.
   c) then heating the tubular product at a first elevated temperature, and radially expanding the tubular product to a second outer diameter;
   d) then heating the expanded tubular product at a second elevated temperature not less than the first elevated temperature; and
   e) then cooling the expanded tubular product to form the noncompliant balloon.

2. The method of claim 1 wherein the extruded tubular product is annealed for about 16 to about 24 hours.

3. The method of claim 1 wherein the extruded tubular product is annealed at about 55° C.

4. The method of claim 3 wherein the extruded tubular product is annealed for about 16 hours.

5. The method of claim 1 wherein the block copolymer is a polyurethane block copolymer, and the tubular product is radially expanded to a blow up ratio of greater than about 6 in c), wherein the blow up ratio is the ratio of the second outer diameter of the expanded tubular product to the first inner diameter of the extruded tubular product.

6. The method of claim 5 wherein the polyurethane block copolymer is a polycarbonate polyurethane block copolymer comprising the product of the reaction of poly(1,6-hexyl 1,2-ethylcarbonate) diol and 4,4'-methylene bisphyenyl diisocyanate (MDI) and a chain extender, and the noncompliant balloon has a rupture pressure of at least about 18 atmospheres, and the tubular product is radially expanded to a blow up ratio of about 7.4 to about 7.8 in c).

* * * * *

UNITED STATES PATENT AND TRADEMARK OFFICE
CERTIFICATE OF CORRECTION

| | |
|---|---|
| PATENT NO. | : 7,892,469 B2 |
| APPLICATION NO. | : 10/802225 |
| DATED | : February 22, 2011 |
| INVENTOR(S) | : Florencia Lim et al. |

It is certified that error appears in the above-identified patent and that said Letters Patent is hereby corrected as shown below:

Drawing page, Sheet 3 of 3, delete current page and insert instead replacement Sheet 3 of 3.

Column 11, line 13, after "300" insert --psi--.

Signed and Sealed this
Sixth Day of March, 2012

David J. Kappos
*Director of the United States Patent and Trademark Office*